United States Patent
Hack et al.

(10) Patent No.: US 9,572,232 B2
(45) Date of Patent: Feb. 14, 2017

(54) BIOSENSING ELECTRONIC DEVICES

(71) Applicant: Universal Display Corporation, Ewing, NJ (US)

(72) Inventors: Michael Hack, Princeton, NJ (US); Ruiqing Ma, Morristown, NJ (US); Emory Krall, Philadelphia, PA (US); Julia J. Brown, Yardley, PA (US)

(73) Assignee: Universal Display Corporation, Ewing, NJ (US)

( * ) Notice: Subject to any disclaimer, the term of this patent is extended or adjusted under 35 U.S.C. 154(b) by 0 days.

(21) Appl. No.: 14/575,281

(22) Filed: Dec. 18, 2014

(65) Prior Publication Data
US 2015/0334808 A1 Nov. 19, 2015

Related U.S. Application Data
(60) Provisional application No. 61/993,377, filed on May 15, 2014.

(51) Int. Cl.
H05B 37/02 (2006.01)
A61M 21/00 (2006.01)
H05B 33/08 (2006.01)
A61N 5/06 (2006.01)

(52) U.S. Cl.
CPC .......... *H05B 37/0227* (2013.01); *A61M 21/00* (2013.01); *H05B 33/0896* (2013.01); *A61M 2021/0044* (2013.01); *A61M 2205/3523* (2013.01); *A61M 2205/587* (2013.01); *A61M 2209/088* (2013.01); *A61M 2230/06* (2013.01); *A61M 2230/08* (2013.01); *A61M 2230/205* (2013.01); *A61M 2230/30* (2013.01); *A61M 2230/50* (2013.01); *A61M 2230/63* (2013.01); *A61M 2230/65* (2013.01); *A61N 5/0618* (2013.01)

(58) Field of Classification Search
USPC ........................................................ 315/297
See application file for complete search history.

(56) References Cited

U.S. PATENT DOCUMENTS

| 4,769,292 A | 9/1988 | Tang et al. |
| 5,247,190 A | 9/1993 | Friend et al. |
| 5,703,436 A | 12/1997 | Forrest et al. |
| 5,707,745 A | 1/1998 | Forrest et al. |

(Continued)

FOREIGN PATENT DOCUMENTS

| EP | 1238981 | 9/2002 |
| JP | 2010/135467 | 6/2010 |

(Continued)

OTHER PUBLICATIONS http://en.wikipedia.org/wiki/F.lux.

(Continued)

*Primary Examiner* — Vibol Tan
(74) *Attorney, Agent, or Firm* — Riverside Law LLP

(57) ABSTRACT

The device consists of measuring aspects of human activity or emotion and then communicating that information to an adjustable lighting device or electronic display (as part of a phone, tablet, computer etc) such that the color temperature (or luminance) of the display or lamp is adjusted to match the mood of the user e.g. warmer in the evening close to the end of the day, and cooler in the morning for productivity.

14 Claims, 3 Drawing Sheets

(56) References Cited

U.S. PATENT DOCUMENTS

| | | | |
|---|---|---|---|
| 5,834,893 | A | 11/1998 | Bulovic et al. |
| 5,844,363 | A | 12/1998 | Gu et al. |
| 6,013,982 | A | 1/2000 | Thompson et al. |
| 6,087,196 | A | 7/2000 | Sturm et al. |
| 6,091,195 | A | 7/2000 | Forrest et al. |
| 6,097,147 | A | 8/2000 | Baldo et al. |
| 6,294,398 | B1 | 9/2001 | Kim et al. |
| 6,303,238 | B1 | 10/2001 | Thompson et al. |
| 6,337,102 | B1 | 1/2002 | Forrest et al. |
| 6,468,819 | B1 | 10/2002 | Kim et al. |
| 7,279,704 | B2 | 10/2007 | Walters et al. |
| 7,431,968 | B1 | 10/2008 | Shtein et al. |
| 7,968,146 | B2 | 6/2011 | Wagner et al. |
| 2002/0047646 | A1* | 4/2002 | Lys .................... H05B 33/0803 315/312 |
| 2003/0230980 | A1 | 12/2003 | Forrest et al. |
| 2004/0174116 | A1 | 9/2004 | Lu et al. |
| 2010/0079508 | A1* | 4/2010 | Hodge .................... G06F 3/013 345/697 |
| 2012/0194976 | A1* | 8/2012 | Golko .................... G06F 1/163 361/679.01 |
| 2012/0206050 | A1* | 8/2012 | Spero .................... B60Q 1/04 315/152 |
| 2012/0271121 | A1* | 10/2012 | Della Torre ......... A61B 5/0059 600/301 |
| 2012/0319593 | A1* | 12/2012 | Jou .................... H05B 33/0869 315/152 |
| 2013/0026452 | A1 | 1/2013 | Kottas et al. |
| 2013/0119354 | A1 | 5/2013 | Ma et al. |
| 2014/0155705 | A1* | 6/2014 | Papadopoulos ..... G06F 19/3481 600/301 |
| 2014/0334653 | A1* | 11/2014 | Luna ...................... G05B 15/02 381/332 |
| 2015/0269009 | A1* | 9/2015 | Faaborg .................. G06F 9/546 719/315 |

FOREIGN PATENT DOCUMENTS

| | | |
|---|---|---|
| WO | 2004/111066 | 12/2004 |
| WO | 2008/044723 | 4/2008 |
| WO | 2008057394 | 5/2008 |
| WO | 2010011390 | 1/2010 |
| WO | 2010/111175 | 9/2010 |

OTHER PUBLICATIONS

U.S. Appl. No. 14/015,526 filed Aug. 30, 2013.

Baldo et al., "Highly Efficient Phosphorescent Emission from Organic Electroluminescent Devices," Nature, vol. 395, 151-154, (1998).

Baldo et al., "Very high-efficiency green organic light-emitting devices based on electrophosphorescence," Appl. Phys. Lett., vol. 75, No. 1, 4-6 (1999).

* cited by examiner

BIOSENSING ELECTRONIC DEVICES

CROSS-REFERENCE TO RELATED APPLICATIONS

This application claims priority to U.S. Provisional Patent Application Ser. No. 61/993,377, filed May 15, 2014, the entire contents of which is incorporated herein by reference in its entirety.

PARTIES TO A JOINT RESEARCH AGREEMENT

The claimed invention was made by, on behalf of, and/or in connection with one or more of the following parties to a joint university corporation research agreement: Regents of the University of Michigan, Princeton University, University of Southern California, and the Universal Display Corporation. The agreement was in effect on and before the date the claimed invention was made, and the claimed invention was made as a result of activities undertaken within the scope of the agreement.

FIELD OF THE INVENTION

The present invention relates to electronic biosensing systems, and particularly to systems that detect or measure physiological parameters of a user and control output from nearby light emitting devices based on the detected or measured physiological parameters.

BACKGROUND

It is well known that the type and amount of light from a light source can variably effect people, both physiologically and psychologically. For example, depending on the desired mood and behavior of people in a room, the type of lighting and the amount of light in the room can be adjusted to achieve the desired mood and behavior from the people in the room. This has been historically done in settings such as in a hospital waiting room or treatment room, in a restaurant dining area, or in a romantic setting of a private home.

However, in each of these cases, the adjustment of light is pre-set, meaning that the output of emitted light is adjusted to a level in hopes of directing or causing a person to behave in a particular way or to reach a desired mood. Unfortunately, the reality of human psychology and physiology is that a person's autonomic nervous system can be affected or triggered very quickly and by a host of other factors. The result is that these existing environments simply cannot adjust to the person's changing physiology and psychology in real time.

This is particularly unfortunate because in today's world, people are not only effected by room or environment lighting, but also by significant use of lighted visual displays integrated into devices such as televisions, computers and phones. For example, it is believed that blue light impairs sleep when digital display screens are used around bedtime. However, there is no system available that can adjust the level or output of blue light to match the real-time physiological state of a subject viewing the digital display as the subject becomes ready for sleep. In another example, it is believed that hyper-stimulation from visual displays can potentially cause photosensitive epilepsy, due to the movement of images on the screen and the bright flashing of light on the screen. However, there is no system available that can adjust the intensity or color temperature of output light to reduce such undesired neurological effects.

Unfortunately, there is no system to take advantage of the highly adjustable output of current lighting and display devices based on real time detection of a person's activity or emotional state. The present invention addresses this need.

SUMMARY OF THE INVENTION

The present invention includes a system for modulating output from a light emitting device in real time. The system includes at least one sensor for detecting at least one measurable parameter associated with a user, at least one light emitting device, and a controller communicatively connected to the at least one sensor and the at least one light emitting device, wherein the controller directs the at least one light emitting device to change an output from the device based on the at least one parameter measured by the at least one sensor.

The present invention also includes a method of modulating the output of a light emitting device in real time. The method includes the steps of associating at least one sensor with a user, sensing at least one measurable parameter pertaining to the user, transmitting a signal to a light emitting device corresponding to the sensed parameter, and modulating the output of the light emitting device based on the transmitted signal.

In one embodiment, the light emitting device output being modulated is spectrum wavelength. In another embodiment, the light emitting device output being modulated is luminance. In another embodiment, the light emitting device output being modulated is color temperature.

In another embodiment, the at least one light emitting device is a lamp. In another embodiment, the at least one light emitting device is a visual display screen. In another embodiment, at least one light emitting device is an organic light-emitting diode (OLED).

In another embodiment, the measurable parameter is selected from the group consisting of heart rate, temperature, degree of motion, coded motion, and a biological molecule.

In another embodiment, the at least one sensor is a heart rate sensor, a temperature sensor, a pressure sensor, a motion sensor or accelerometer a galvanic skin response sensor, a blood or tissue gas sensor such as a blood oxygen sensor, a blood analyte sensor, or a neural activity sensor.

In another embodiment, the at least one sensor is housed in a wearable device. In another embodiment, the wearable device is a wrist watch. In another embodiment, the at least one sensor is implanted in the user.

In another embodiment, the controller is connected to one or both of the at least one sensor and at least one light emitting device by a wireless communications network. In another embodiment, the controller is integrated with the light emitting device. In another embodiment, the light emitting device is a computing device having a visual display screen. In another embodiment, the controller is integrated with at least one sensor in the wearable device. In another embodiment, the controller is positioned in a centralized hub. In another embodiment, the system further includes at least one microcontroller integrated with the at least one sensor, and at least one microcontroller integrated with the at least one light emitting device, wherein the microcontroller integrated with the at least one sensor communicates with the microcontroller integrated with the at least one light emitting device via the controller hub. In another embodiment, the controller hub directs output of a plurality of light emitting devices in one or more rooms of an indoor facility.

DETAILED DESCRIPTION

The present invention relates to a system that can measure physiological parameters of a subject in real time, and utilize that information about the subject to determine the activity level or emotional state of the subject so that lighting devices in the vicinity of the subject can adjust the output of light to either match or alter the mood of the subject in real time. As contemplated herein, the system includes at least one sensor to measure at least one physiological parameter, at least one light emitting device, a communications network, and at least one controller to direct the light emitting device to adjust light output based on the measured physiological parameter, via the communications network. Further, the present invention also relates to a method of modulating the output of a light emitting device in real time.

Figure 1:
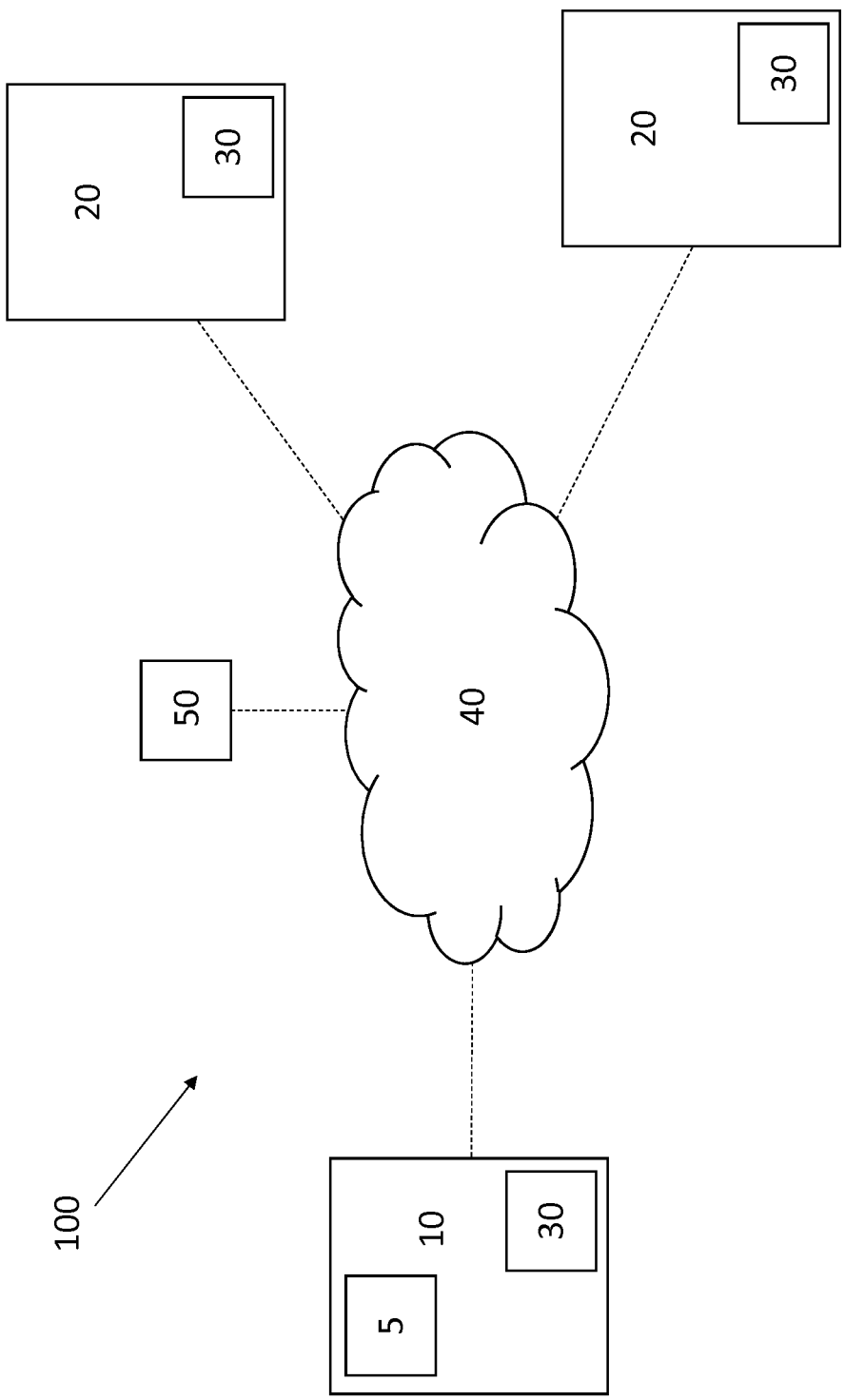
FIG. 1 is a schematic of an exemplary communications network configuration, incorporating an optional controller hub for receiving signals from a biosensing device and directing output from at least one light emitting device.

In one embodiment and as shown in FIG. 1, system 100 includes at least one sensor 5 housed within at least one wearable or at least partially implantable biosensing device 10, at least one light emitting device 20, and a communications network 40. A controller, microcontroller or driver 30 may be optionally integrated with any of biosensing devices 10 or light emitting devices 20. Accordingly, biosensing device 10 may communicate directly with any one of light emitting devices 20 via network 40. Optionally or additionally, system 100 may include a controller hub 50 for receiving information from biosensing devices 10 and directing any of light emitting devices 20 to adjust or alter its output based on the received information from one or more biosensing devices 10. System 100 may be used in any setting, including a single room or multiple rooms of a home, office or other building, or it may be used in a mobile setting, such as within an automobile, passenger train or airplane.

As contemplated herein, each of biosensing devices 10 include one or more sensors 5 for detecting or measuring at least one physiological parameter. As contemplated herein, exemplary physiological parameters include, without limitation, electrodermal activity, heart rate and heart rate variability, brain activity, eye activity, temperature, motion, quantitative or qualitative detection of biomarkers or analytes such as cortisol, melatonin and other hormones associated with circadian rhythm, and the like. Accordingly, sensors 5 may be any type of sensor suitable for detecting or measuring such physiological parameters of a subject. Sensors 5 may be positioned within biosensing devices 10 such that they are proximate to or substantially in contact with an exterior surface of a subject, or such that they may be at least partially implanted within a subject.

Without limitation, sensors 5 may be any type of sensor, including a heart rate sensor, a temperature sensor, a pressure sensor, a motion sensor or accelerometer a galvanic skin response sensor, a blood or tissue gas sensor such as a blood oxygen sensor, a blood analyte sensor, a neural activity sensor, an electroencephalography sensor, an electrocardiography sensor, an electrooculography sensor, an electromyography sensor, a camera, an eye tracking lens and other eye tracking systems, or any other wearable or insertable sensor as would be understood by those skilled in the art. Alternatively, one or more sensors 5 is not worn or inserted, but rather may be positioned locally to the subject, such as a camera on a computing device that is capable of viewing and capturing images of the subject. In this alternative embodiment, the camera or other sensor may be integrated with the light emitting device 20, or it may be a separate device that is suitably positioned within the local environment to view and/or sense the physiological parameter of the subject.

Biosensing devices 10 may include wearable devices or accessories, such as a watch, a ring or other jewelry item, glasses and the like. Further, biosensing devices 10 may be any device not otherwise considered wearable, but is at least temporarily attachable to the subject, at any desired location or position on the subject. Biosensing devices 10 may also be an article of clothing, such as a headband or wristband, a sock, a glove, a hat, a shirt, shorts, pants, a shoe and the like. Further, biosensing device 10 may be an internal probe or include a probe that is at least partially insertable into a subject, such that the sensor 5 within the probe can be positioned within the subject. Alternatively, biosensing devices 10 may be positioned locally but not in contact with the subject, such as a remotely positioned camera for recording images of the subject or body part of the subject, such as the eye. Biosensing devices 10, in addition to sensors 5 and optionally controller 30, may include at least one processor, input and output devices, as well as all hardware and software typically found on devices for storing data and running programs, and for sending and receiving data over a network.

Light emitting devices 20 may be any type of unit having a light source that is capable of adjusting its output, including partial adjustment of output including color, or fully turning on output and fully turning off output. For example and without limitation, light emitting devices 20 may include any type of room lighting, such as a reading lamp or sconce, a table lamp, a floor lamp, overhead lighting and the like. Further, light emitting devices 20 may include visual displays of computing or other electronic devices, such as desktop or mobile devices, laptops, tablets, wireless digital/cellular phones, televisions or other thin client devices as would be understood by those skilled in the art. As contemplated herein, the light source of light emitting devices 20 may utilize any type of artificial lighting, including incandescent lamps, halogen lamps, fluorescent lamps, compact fluorescent lamps, cold cathode fluorescent lamps, high-intensity discharge lamps, light-emitting diodes (LEDs), organic light-emitting diodes (OLEDs), polymer light-emitting diodes (PLEDs), and the like. For visual displays, such lighting sources may include, without limitation, cathode ray tubes, plasma displays, liquid crystal displays, LEDs, OLEDs, electroluminescent displays (ELDs), holographic displays, electronic paper, and the like.

As contemplated herein, adjusting the output of light emitting devices 20 may include fully turning the device on to emit light, or fully turning the device off so that no light is emitted. Further, the output of light emitting devices 20 can be partially adjusted, so that at least one aspect of emitted light is altered. For example, in one embodiment, the spectrum wavelength of the output light from at least one light emitting device 20 is at least partially altered. In another embodiment, the luminance of the output light from at least one light emitting device 20 is at least partially altered. In yet another embodiment, the color temperature of the output light from at least one light emitting device 20 is at least partially altered.

In certain embodiments, system 100 may include controller hub 50 for receiving information from one or more biosensing devices 10 and directing one or more light emitting devices 20 to alter its light output based on the information received from the one or more biosensing devices 10. As contemplated herein, controller hub 50 may be a standard computing device having at least one processor, standard input and output devices, as well as all hardware and software typically found on computing devices for storing data and running programs, and for sending and receiving data over a network. Controller hub 50 may be scalable and include multiple computing units covering a large area. Controller hub 50 may also be connected directly or via a network to one or more databases, such as for additional storage backup, and to allow for the communication of files, software, and any other data format between two or more computing devices. In one embodiment, controller hub 50 is a stationary unit positioned centrally within an artificially lit room or dwelling. In another embodiment, controller hub 50 may be portable or mobile. For example, controller hub 50 may be a smart phone carried by a subject, such that it directs the light output of one or more locally positioned light emitting devices 20 based on information received from at least one biosensing device 10 worn by the subject.

System 100 may also have associated therewith a software platform that may operate as a local or remote executable software platform, executable by any of biosensing devices 10, light emitting devices 20 and controller hub 50 (also referred to herein collectively as computing devices). As contemplated herein, any other computing device as would be understood by those skilled in the art may be used with the system, including desktop or mobile devices, laptops, tablets, wireless digital/cellular phones, televisions or other thin client devices as would be understood by those skilled in the art.

For example, the computer operable component(s) of the system may reside entirely on a single computing device, or may reside on any number of devices within the system. Any computing devices contemplated herein may generally include at least one processor, standard input and output devices, as well as all hardware and software typically found on computing devices for storing data and running programs, and for sending and receiving data over a network, if needed. The computing device(s) may also be connected directly or via a network to remote databases, such as for additional storage backup, and to allow for the communication of files, email, software, and any other data format between two or more computing devices. There are no limitations to the number, type or connectivity of the databases utilized by the system of the present invention.

The communications network 40 can be a wide area network and may be any suitable networked system understood by those having ordinary skill in the art, such as, for example, an open, wide area network (e.g., the internet), an electronic network, an optical network, a wireless network, a physically secure network or virtual private network, and any combinations thereof. The communications network 40 may also include any intermediate nodes, such as gateways, routers, bridges, internet service provider networks, public-switched telephone networks, proxy servers, firewalls, and the like, such that the communications network may be suitable for the transmission of information items and other data throughout system 100.

Further, the communications network may also use standard architecture and protocols as understood by those skilled in the art, such as, for example, a packet switched network for transporting information and packets in accordance with a standard transmission control protocol/Internet protocol ("TCP/IP"). Any of the computing devices may be communicatively connected into the communications network through, for example, a traditional telephone service connection using a conventional modem, an integrated services digital network ("ISDN"), a cable connection including a data over cable system interface specification ("DOCSIS") cable modem, a digital subscriber line ("DSL"), a Ti line, or any other mechanism as understood by those skilled in the art. Additionally, the system may utilize any conventional operating platform or combination of platforms (Windows, Mac OS, Unix, Linux, Android, etc.) and may utilize any conventional networking and communications software as would be understood by those skilled in the art.

To protect data, an encryption standard may be used to protect files from unauthorized interception over the network. Any encryption standard or authentication method as may be understood by those having ordinary skill in the art may be used at any point in the system of the present invention. For example, encryption may be accomplished by encrypting an output file by using a Secure Socket Layer (SSL) with dual key encryption. Additionally, the system may limit data manipulation, or information access.

As mentioned previously, the system may include an application software, which may be managed by a local or remote computing device, such as controller hub 50. The software may include a software framework or architecture that optimizes ease of use of at least one existing software platform, and that may also extend the capabilities of at least one existing software platform. The application architecture may approximate the actual way users organize and manage electronic files, and thus may organize use activities in a natural, coherent manner while delivering use activities through a simple, consistent, and intuitive interface within each application and across applications. The architecture may also be reusable, providing plug-in capability to any number of applications, without extensive re-programming, which may enable parties outside of the system to create components that plug into the architecture. Thus, software or portals in the architecture may be extensible and new software or portals may be created for the architecture by any party.

The system may provide software accessible to one or more users to perform one or more functions. Such applications may be available at the same location as the user, or at a location remote from the user. Each application may provide a graphical user interface (GUI) for ease of interaction by the user with information resident in the system. A GUI may be specific to a user, set of users, or type of user, or may be the same for all users or a selected subset of users. The system software may also provide a master GUI set that allows a user to select or interact with GUIs of one or more other applications, or that allows a user to simultaneously access a variety of information otherwise available through any portion of the system.

The system software may also be a portal or SaaS that provides, via the GUI, remote access to and from the system of the present invention. The software may include, for example, a network browser, as well as other standard applications. The software may also include the ability, either automatically based upon a user request in another application, or by a user request, to search, or otherwise retrieve particular data from one or more remote points, such as on the internet or from a limited or restricted database. The software may vary by user type, or may be available to only a certain user type, depending on the needs of the system. Users may have some portions, or all of the application software resident on a local computing device, or may simply have linking mechanisms, as understood by those skilled in the art, to link a computing device to the software running on a central server via the communications network, for example. As such, any device having, or having access to, the software may be capable of uploading, or downloading, any information item or data collection item, or informational files to be associated with such files.

Presentation of data through the software may be in any sort and number of selectable formats. For example, a multi-layer format may be used, wherein additional information is available by viewing successively lower layers of presented information. Such layers may be made available by the use of drop down menus, tabbed folder files, or other layering techniques understood by those skilled in the art or through a novel natural language interface as described herein. Formats may also include AutoFill functionality, wherein data may be filled responsively to the entry of partial data in a particular field by the user. All formats may be in standard readable formats, such as XML. The software may further incorporate standard features typically found in applications, such as, for example, a front or "main" page to present a user with various selectable options for use or organization of information item collection fields.

The system software may also include standard reporting mechanisms, such as generating a printable results report, or an electronic results report that can be transmitted to any communicatively connected computing device, such as a generated email message or file attachment. Likewise, particular results of the aforementioned system can trigger an alert signal, such as the generation of an alert email, text or phone call, to alert a user of the particular results. Further embodiments of such mechanisms are described elsewhere herein or may standard systems understood by those skilled in the art.

In certain embodiments, controller hub 50, or alternatively light emitting devices 20, are programmed to execute the aforementioned system software to receive and interpret data received from biosensing devices 10. Such data includes all signals collected from sensors 5 that are indicative of a physiological parameter detected or otherwise measured by sensors 5. Further, the system is programmed to receive and interpret coded motion of sensor 5 in biosensing device 10. By non-limiting example, such coded motion may be a quickly executed, sequential two-shake motion to be indicative of the subject desiring a local light emitting device in the vicinity of the subject to be turned on.

Further still, it should be appreciated that the system software may be programmed to determine more complex emotional states, using programmed logic that interprets the received signal of two or more physiological parameters to arrive at a determination of the particular emotional state of the subject. Accordingly, the system of the present invention may include any algorithm understood by those skilled in the art that utilizes and equates the value (or information item) of at least one measured physiological parameter to a physiological, psychological or emotional state of the subject, such that the system of the present invention may alter the output of light from at least one light emitting device in the vicinity of the subject based on the determination of that subject's state. It should also be appreciated that the system is not limited to any particular combination of factors, or weighting of factors, in determining the output of light from the light emitting device. For example, the system may include a scoring metric, or algorithm, by which to weight each information item from each sensor in the system, and to calculate a total value or score that is determinative of a desired light output. It should be appreciated that the values designated for each information item from any particular sensor may vary according to the target subject or user group for which control of light output is desired. Further, the number or combination of information items from the sensors will also effect the values designated. Further, the final score may be set as a threshold value, where a score of equal to or above a designated value indicates that light output should be altered. Alternatively, final score ranges can be used to designate categories of light output. It should be appreciated that any system algorithm used is not limited to any predetermined value, number or other nomenclature.

Figure 2:
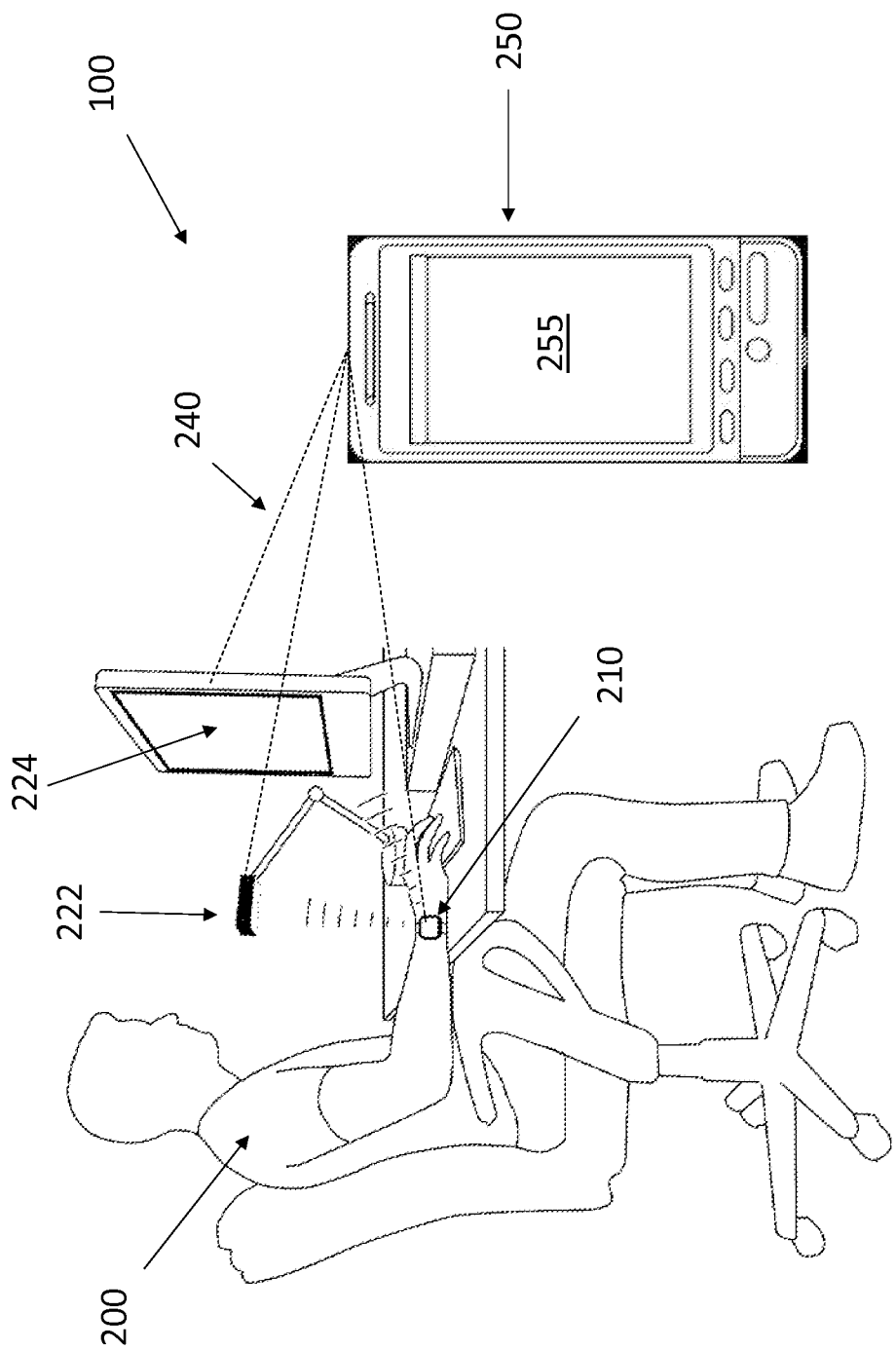
FIG. 2 is a schematic of a person or subject with a wearable sending device communicating with a table lamp or visual display via a smart phone within a wireless network, in accordance with the invention.

Accordingly, in one exemplary embodiment and as illustrated in FIG. 2, light emitting device 20 may be a personal lamp or general illumination lamp, such as an LED or OLED lamp that can alter any or all of the output light spectral wavelength, luminance or intensity, or the color temperature. In another exemplary embodiment, light emitting device 20 is a smart phone or tablet having a LCD backlight or an OLED screen that can alter any or all of the output light spectral wavelength, luminance or intensity, or the color temperature.

For example, as shown in FIG. 2, a subject 200 may wear a biosensing device in the form of a watch 210 having an integrated heart rate sensor (not shown) positioned proximate to the wrist of subject 200. Subject 200 is sitting at a desk having positioned thereon light emitting devices in the form of a table lamp 222 and a visual display 224. Each of watch 210, table lamp 222 and visual display 224 are communicatively connected to smart phone 250 via a wireless network 240 (dashed lines). Smart phone 250 has resident therein an executable software application directed to interpretation of physiological parameter data received from watch 210 and the subsequent control of light output from table lamp 222 and visual display 224. Watch 210 detects the heart rate of subject 200. The watch 210 transmits data to smart phone 250 that is indicative of the heart rate of subject 200. Accordingly, when smart phone 250 logic determines that the heart rate of subject 200 has slowed (e.g., the subject is becoming sleepy), smart phone 250 signals one or both of table lamp 222 and visual display 224 to reduce the emission of blue light, thereby altering the light output of one or both of table lamp 222 and visual display 224 to be more "warm" white light.

In another example, the subject may have a biosensing device in the form of a probe that is inserted into the bloodstream of a subject, wherein the probe includes an electrochemical immunosensor capable of detecting a change in electrical properties of a functionalized substrate that is correlated to quantifiable levels of a biomarker, such as cortisol, in the blood. Accordingly, when the smart phone controller receives the biosensing probe data and determines the amount of cortisol in the blood, the controller software can match the detected levels of cortisol against a desired cortisol level, for example based on time of day, and then adjust long and short spectrum wavelength light as predicated.

Alternatively, table lamp 222 and visual display 224 are not in the vicinity of subject 200, and smart phone 240 is communicatively connected to watch 210 worn by subject 200. In this embodiment, smart phone 240 also constitutes the light emitting device, having its own visual display 255. Accordingly, smart phone 250 functions as both the controller and the light emitting device, such that when smart phone 250 receives data from watch 210 that is indicative of a slowing heart rate in subject 200, smart phone 250 can reduce the luminance emitted from visual display 255 and/or reduce the amount of blue light emitted from visual display 255.

In a further alternative embodiment, a device incorporating a visual display, such a tablet computer, functions as the biosensing device, light emitting device and controller within a single unit. For example, the tablet computer may include a camera that measures the number and/or duration of blinks of a subject's eye. When the tablet computer tracks an eye blinking rate that is greater than a threshold value, or the proportion of time that the eyes are closed is greater than a threshold value, the tablet computer alters the light emitted from its visual display and/or any other light emitting device in the vicinity of the subject.

In another embodiment, system 100 may support multiple subjects, such as multiple family members in a dwelling, or multiple employees in an office space. System 100 may account for multiple subjects by employing channel-sharing wireless protocols to enable the transmission of data from multiple users and multiple sensors to the controller hub, wherein a plurality of light emitting devices are adjusted per the total or flow of received and interpreted biosensing data across multiple subjects. The channel sharing protocols include ad-hoc CSMA (carrier sense multiple access) protocol and time-slotted TDMA (time division multiple access) reader-mediated protocol, or any other sharing protocols as would be understood by those skilled in the art. It should be appreciated that when there are multiple users providing physiological state input into the system, the controller may control light output via algorithms specifically designed for multiple users, including determinations of an average state of all users, the first user to be present in the room or other environment, age based selection, or other criteria by which to determine light output based on the presence of multiple users.

In yet another embodiment, system 100 may include a learning or instructional logic to establish a baseline physiological state that is particular to a specific subject, or to a group of users (such as a family household). For example, system 100 may include a learning protocol in which system 100 collects physiological parameter data over a desired time interval, and likewise learns the typical light emitting device output preferred by the subject over the course of the time interval. Once this data is collected, the subject may confirm for the system that the collected data is representative of a preferred physiological or emotional state. Alternatively or additionally, the system software may include one or more questions answerable by the subject in order to determine a baseline state. Then, when the system later detects a change in this data pattern received from the biosensing devices, the system can begin to alter the output of the light emitting devices to bring the physiological parameters back closer to the desired baseline values. It should be appreciated that such programming, or any programming described herein, may include user overrides, at the individual subject or user group level, to reset or remove any undesired adjustments of light emitting devices.

Figure 3:
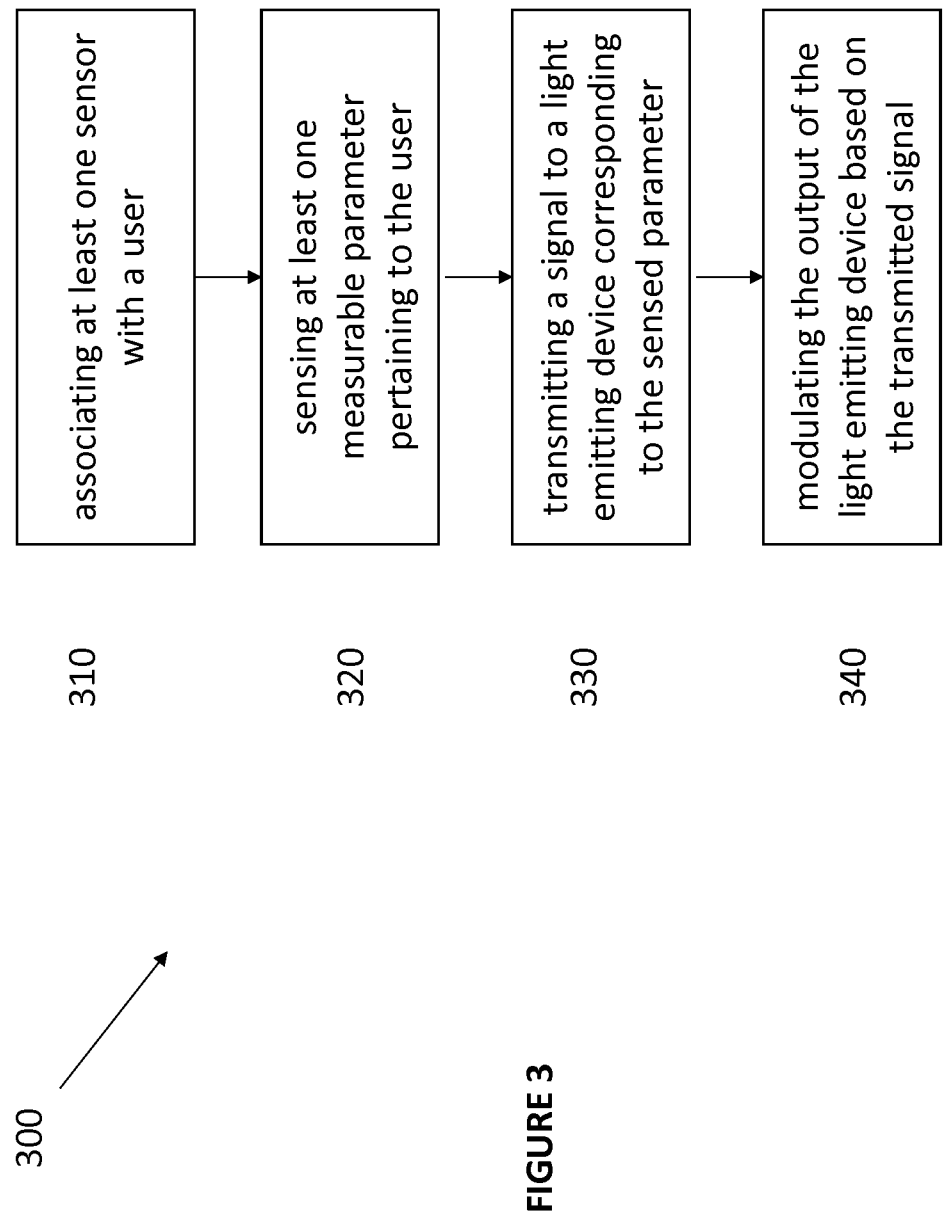
FIG. 3 is a flow chart of an exemplary method in accordance with the present invention.

As contemplated herein, the present invention also includes a method of modulating the output of a light emitting device. The method may include use of a biosensing device having a sensor integrated therewith, a light emitting device having an output of light therefrom, and a controller for directing the output of light from the light emitting device based on data collected from the biosensing device. As shown in FIG. 3, the method 300 includes the steps of associating at least one sensor with a user 310, sensing at least one measurable parameter pertaining to the user 320, transmitting a signal to a light emitting device corresponding to the sensed parameter 330, and modulating the output of the light emitting device based on the transmitted signal 340. It should be appreciated that the methods of the present invention may include use of any sensor, biosensing device design, light emitting device, controller hub and network as described herein. Furthermore, the methods of the present invention may be used to improve the physiological, psychological or emotional state of a subject by detecting a physiological parameter indicative of an undesirable state, and adjusting the output of light from a light emitting device that is in the vicinity of the subject, such that the altered output of light improves the physiological, psychological or emotional state of the subject.

It is understood that the various embodiments described herein are by way of example only, and are not intended to limit the scope of the invention. For example, many of the materials and structures described herein may be substituted with other materials and structures without deviating from the spirit of the invention. The present invention as claimed may therefore include variations from the particular examples and preferred embodiments described herein, as will be apparent to one of skill in the art. It is understood that various theories as to why the invention works are not intended to be limiting.

We claim:

1. A system for modulating output from a light emitting device in real time, comprising:
   at least one sensor for detecting at least one measurable physiological parameter associated with a user;
   at least one light emitting device; and
   a controller communicatively connected to the at least one sensor and the at least one light emitting device,
   wherein the controller directs the at least one light emitting device to change an output from the at least one light emitting device based on the at least one physiological parameter measured by the at least one sensor, and
   wherein the at least one sensor is selected from the group consisting of a sensor in contact with the user, a heart rate sensor, a pressure sensor, a galvanic skin response sensor, a blood or tissue gas sensor, a blood analyte sensor, and a neural activity sensor,
   wherein the output is selected from the group consisting of spectrum wavelength and color temperature, and
   wherein the light emitting device is a visual display screen.

2. The system of claim 1, wherein the light emitting device comprises an organic light-emitting diode (OLED).

3. The system of claim 1, wherein the measurable physiological parameter is selected from the group consisting of heart rate, coded motion, and a biological molecule.

4. The system of claim 1, wherein the at least one sensor is housed in a wearable device.

5. The system of claim 4, wherein the wearable device is a wrist watch.

6. The system of claim 1, wherein the at least one sensor is implanted in the user.

7. The system of claim 1, wherein the controller is connected to one or both of the at least one sensor and at least one light emitting device by a wireless communications network.

8. The system of claim 1, wherein the controller is integrated with the light emitting device.

9. The system of claim 4, wherein the controller is integrated with at least one sensor in the wearable device.

10. The system of claim 1, wherein the controller is positioned in a centralized hub.

11. The system of claim 10, further comprising:
   at least one microcontroller integrated with the at least one sensor; and
   at least one microcontroller integrated with the at least one light emitting device;
   wherein the microcontroller integrated with the at least one sensor communicates with the microcontroller integrated with the at least one light emitting device via the controller hub.

12. The system of claim 1, wherein the at least one sensor is a plurality of sensors for detecting at least one measurable physiological parameter from each of a plurality of users, such that the controller directs the at least one light emitting device to change an output from the device based on at least one physiological parameter measured from each of the plurality of users.

13. The system of claim 1, wherein the controller directs output of a plurality of light emitting devices in one or more rooms of an indoor facility.

14. A method of modulating an output of a light emitting device in real time, comprising the steps of:
   associating at least one sensor with a user;
   sensing at least one measurable physiological parameter pertaining to the user;
   transmitting a signal to a light emitting device corresponding to the sensed physiological parameter; and
   modulating the output of the light emitting device based on the transmitted signal,
   wherein the at least one sensor is selected from the group consisting of a sensor in contact with the user, a heart rate sensor, a pressure sensor, a galvanic skin response sensor, a blood or tissue gas sensor, a blood analyte sensor, and a neural activity sensor, and
   wherein the modulated light emitting device output is selected from the group consisting of spectrum wavelength and color temperature, and
   wherein the light emitting device is a visual display screen.

* * * * *